US006380371B1

(12) United States Patent
Sassetti et al.

(10) Patent No.: US 6,380,371 B1
(45) Date of Patent: Apr. 30, 2002

(54) ENDOGLYCAN: A NOVEL PROTEIN HAVING SELECTIN LIGAND AND CHEMOKINE PRESENTATION ACTIVITY

(75) Inventors: Christopher M. Sassetti, Richmond; Steven D. Rosen, San Francisco, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/394,645

(22) Filed: Sep. 13, 1999

Related U.S. Application Data

(60) Provisional application No. 60/111,663, filed on Dec. 10, 1998.

(51) Int. Cl.[7] .......................... C07H 21/04; C07H 1/00
(52) U.S. Cl. .................. 536/23.1; 536/23.5; 530/380; 530/350
(58) Field of Search .................... 536/23.1, 23.5; 435/320.1, 71.1; 530/350, 300, 380

(56) References Cited

U.S. PATENT DOCUMENTS

| 5,705,623 A | | 1/1998 | Wiggins et al. | |
| 5,723,315 A | * | 3/1998 | Jacobs et al. | ............... 435/69.1 |

FOREIGN PATENT DOCUMENTS

| EP | 365894 A | * | 5/1990 | |

OTHER PUBLICATIONS

Kershaw et al. J. Biol. Chem. 270: 29439–29446, 1995.*
Patrassi et al. Folia Haematol., Leipzig 117: 369–376, 1990.*
Lehninger AL. Principles of Biochemistry, Worth Publishers, Inc., New York, Chapter 27, pp. 793–836, 1982.*
Adams et al. Nature Genetics 4: 256–267, 1993, abstract.*
Kerjaschki, et al. (1984), "Identification and Characterization of Podocalyxin–the major Sialoprotein of the Renal Glomerular Epithelial Cell," *Journal of Cell Biology* vol. 98:1591–1596.
Kershaw, et al. (1997), "Molecular Cloning and Characterization of Human Podocalyxin–like Protein," *Journal of Biological Chemistry* vol. 272(25):15708–15714.
Middleton, et al. (1997), "Transcytosis and Surface Presentation of IL–8 by Venular Endothelial Cells," *Cell* vol. 91:385–395.
McNagny, et al. (1997), "Thrombomucin, a Novel Cell Surface Protein that Defines Thrombocytes and Multipotent Hematopoietic Progenitors," *Journal of Cell Biology* vol. 138(6):1395–1407.
Sassetti, et al. (1998), "Identification of Podocalyxin–like Protein as a High Endothelial Venule Ligand for L–Selectin: Parallels to CD34," *J. Exp. Med.* vol. 187(12):1965–1975.

* cited by examiner

*Primary Examiner*—S. Devi
(74) *Attorney, Agent, or Firm*—Paula A. Borden; Bret Field; Bozicevic, Field & Francis, LLP

(57) ABSTRACT

Nucleic acid compositions encoding novel endoglycan proteins, as well as the novel endoglycan proteins, are provided. Also provided are methods of producing the subject nucleic acid and protein compositions. The subject polypeptide and nucleic acid compositions find use in a variety of applications, including diagnostic and therapeutic agent screening applications, as well as in treatment therapies for disease conditions associated with endoglycan activity. In particular, methods of treating diseases associated with endoglycan selectin binding activity and/or chemokine presenting activity are provided, where such diseases include inflammation and the like.

5 Claims, 1 Drawing Sheet

Figure 1

```
   1 CCAGTTCCGGCACGAGGACCATGGGCCGGCTGCTGCGGGCCGCCCGGCTGCCGCCGCTGC    60
                        M  G  R  L  L  R  A  A  R  L  P  P  L  L
  61 TTTCGCCGCTGCTGCTTCTGCTGGTTGGGGGAGCGTTCCTGGGTGCCTGTGTGGCTGGGT   120
      S  P  L  L  L  L  V  G  G  A  F  L  G  A  C  V  A  G  S
 121 CTGATGAGCCTGGCCCAGAGGGCCTCACCTCCACCTCCCTGCTAGACCTCCTGCTGCCCA   180
      D  E  P  G  P  E  G  L  T  S  T  S  L  L  D  L  L  P  T
 181 CTGGCTTGGAGCCACTGGACTCAGAGGAGCCTAGTGAGACCATGGGCCTGGGAGCTGGGC   240
      G  L  E  P  L  D  S  E  E  P  S  E  T  M  G  L  G  A  G  L
 241 TGGGAGCCCCTGGCTCAGGCTTCCCCAGCGAAGAGAATGAAGAGTCTCGGATTCTGCAGC   300
      G  A  P  G  S  G  F  P  S  E  E  N  E  E  S  R  I  L  Q  P
 301 CACCACAGTACTTCTGGGAAGAGGAGGAAGAGCTGAATGACTCAAGTCTGGACCTGGGAC   360
      P  Q  Y  F  W  E  E  E  E  L  N  D  S  S  L  D  L  G  P
 361 CCACTGCAGATTATGTTTTTCCTGACTTAACTGAGAAGGCAGGTTCCATTGAAGACACTA   420
      T  A  D  Y  V  F  P  D  L  T  E  K  A  G  S  I  E  D  T  S
 421 GCCAGGCTCAAGAGCTGCCAAACCTCCCCTCTCCCTTGCCCAAGATGAATCTGGTTGAGC   480
      Q  A  Q  E  L  P  N  L  P  S  P  L  P  K  M  N  L  V  E  P
 481 CTCCCTGGCATATGCCTCCCAGAGAGGAGGAAGAAGAGGAAGAGGAAGAGGAGGAGAGGG   540
      P  W  H  M  P  P  R  E  E  E  E  E  E  E  E  E  E  E  R  E
 541 AGAAGGAAGAGGTAGAGAAACAAGAGGAGGAGGAAGAGGAGGAGCTGCTCCCTGTGAATG   600
      K  E  E  V  E  K  Q  E  E  E  E  E  E  L  L  P  V  N  G
 601 GATCCCAAGAAGAAGCCAAGCCTCAGGTCCGTGACTTTTCTCTCACCAGCAGCAGCCAGA   660
      S  Q  E  E  A  K  P  Q  V  R  D  F  S  L  T  S  S  S  Q  T
 661 CCCCAGGGGCCACCAAAAGCAGGCATGAAGACTCCGGGGACCAGGCCTCATCAGGTGTGG   720
      P  G  A  T  K  S  R  H  E  D  S  G  D  Q  A  S  S  G  V  E
 721 AGGTGGAGAGCAGCATGGGGCCCAGCTTGCTGCTGCCTTCAGTCACCCCAACTACAGTGA   780
      V  E  S  S  M  G  P  S  L  L  L  P  S  V  T  P  T  T  V  T
 781 CTCCGGGGGACCAGGACTCCACCAGCCAAGAGGCAGAGGCCACAGTGCTGCCAGCTGCAG   840
      P  G  D  Q  D  S  T  S  Q  E  A  E  A  T  V  L  P  A  A  G
 841 GGCTTGGGGTAGAGTTCGAGGCTCCTCAGGAAGCAAGCGAGGAAGCCACTGCAGGAGCAG   900
      L  G  V  E  F  E  A  P  Q  E  A  S  E  E  A  T  A  G  A  A
 901 CTGGTTTGTCTGGCCAGCACGAGGAGGTGCCGGCCTTGCCTTCATTCCCTCAAACCACAG   960
      G  L  S  G  Q  H  E  E  V  P  A  L  P  S  F  P  Q  T  T  A
 961 CTCCCAGTGGGGCCGAGCACCCAGATGAAGATCCCCTTGGCTCTAGAACCTCAGCCTCTT  1020
      P  S  G  A  E  H  P  D  E  D  P  L  G  S  R  T  S  A  S  S
1021 CCCCACTGGCCCCTGGAGACATGGAACTGACACCTTCCTCTGCTACCTTGGGACAAGAAG  1080
      P  L  A  P  G  D  M  E  L  T  P  S  S  A  T  L  G  Q  E  D
1081 ATCTCAACCAGCAGCTCCTAGAAGGGCAGGCAGCTGAAGCTCAATCCAGGATACCCTGGG  1140
      L  N  Q  Q  L  L  E  G  Q  A  A  E  A  Q  S  R  I  P  W  D
1141 ATTCTACGCAGGTGATCTGCAAGGACTGGAGCAATCTGGCTGGGAAAAACTACATCATTC  1200
      S  T  Q  V  I  C  K  D  W  S  N  L  A  G  K  N  Y  I  I  L
1201 TGAACATGACAGAGAACATAGACTGTGAGGTGTTCCGGCAGCACCGGGGGCCACAGCTCC  1260
      N  M  T  E  N  I  D  C  E  V  F  R  Q  H  R  G  P  Q  L  L
1261 TGGCCCTGGTGGAAGAGGTGCTGCCCCGCCATGGCAGTGGCCACCATGGGGCCTGGCACA  1320
      A  L  V  E  E  V  L  P  R  H  G  S  G  H  H  G  A  W  H  I
1321 TCTCTCTGAGCAAGCCCAGCGAGAAGGAGCAGCACCTTCTCATGACACTGGTGGGCGAGC  1380
      S  L  S  K  P  S  E  K  E  Q  H  L  L  M  T  L  V  G  E  Q
1381 AGGGGGGTGGTGCCCACTCAAGATGTCCTTTTCCATGCTGGGTGACATCCGCAGGAGCCTGG  1440
      G  V  V  P  T  Q  D  V  L  R  R  S  M  L  G  D  I  R  R  S  L  E
1441 AGGAGATTGGCATCCAGAACTATTCCACAACCAGCAGCTGCCAGGCGCGGGCCAGCCAGG  1500
      E  I  G  I  Q  N  Y  S  T  T  S  S  C  Q  A  R  A  S  Q  V
1501 TGCGCAGCGACTACGGCACGCTCTTCGTGGTGCTGGTGGTCATTGGGGCCATCTGCATCA  1560
      R  S  D  Y  G  T  L  F  V  V  L  V  V  I  G  A  I  C  I  I
1561 TCATCATTGCGCTTGGCCTGCTCTACAACTGCTGGCAGCGCCGGCTGCCCAAGCTCAAGC  1620
      I  I  I  A  L  G  L  L  Y  N  C  W  Q  R  R  L  P  K  L  K  H
1621 ACGTGTCGCACGGCGAGGAGCTGCGCTTCGTGGAGAACGGCTGCCACGACAACCCCACGC  1680
      V  S  H  G  E  E  L  R  F  V  E  N  G  C  H  D  N  P  T  L
1681 TGGACGTGGCCAGCGACAGCCAGTCGGAGATGCAGGAGAAGCACCCCAGCCTGAACGGCG  1740
      D  V  A  S  D  S  Q  S  E  M  Q  E  K  H  P  S  L  N  G  G
1741 GCGGGGCCCTCAACGGCCCGGGGAGCTGGGGGGCGCTCATGGGGGGCAAGCGGGACCCCG  1800
      G  A  L  N  G  P  G  S  W  G  A  L  M  G  G  K  R  D  P  E
1801 AGGACTCGGACGTGTTCGAGGAGGACACGCACCTGTGAGCGCAGCGAGGCGCAGGCCGAG  1860
      D  S  D  V  F  E  E  D  T  H  L  *    (SEQ ID NO:02)
1861 TGGGCCGCCAGGACCAAGCGAGGTGGACCCCGAAACGGACGGCCCGGAGCCCGCACCAGC  1920
1921 CCCGCGCCTACCCGGCCGCCCCCGCGCCTGGCCCTCGGCGCGGGCTCCTTCCCGCTTCCC  1980
1981 CCGACTTCACACGGCGGCTTCGGACCAACTCCCTCACTCCCGCCCGAGGGGCAGGCCTCA  2040
2041 AAGCCCGCCTTGGCCCCGCTTTCCCGCCCCTGAACCCCGGCCCCGCGGGCGGCGGCGCG  2100
2101 CTTCCTCGCGCCCGGGACTCAATTAAACCCGCCCGGAGACCACGCGGGCCCAGCGAAAAA  2160
2161 AAAAAAAAAAAAAAAAAAAAAAAAAAAAAAAAAAAAAAAAAAAAAAAAAAAAAAAAAAAA  2220
2221 AAAAAAAAAAAAAAAAAAAAAAAAAAAAAAAAAAAAAAAAAAAAAAAA  2269 (SEQ ID NO:01)
```

ENDOGLYCAN: A NOVEL PROTEIN HAVING SELECTIN LIGAND AND CHEMOKINE PRESENTATION ACTIVITY

CROSS REFERENCE TO RELATED APPLICATIONS

Pursuant to 35 U.S.C. §119 (e), this application claims priority to the filing date of the U.S. Provisional Patent Application Ser. No. 60/111,663 filed Dec. 10, 1998, the disclosure of which is herein incorporated by reference.

ACKNOWLEDGMENT OF GOVERNMENT SUPPORT

This invention was made with Government support under Grant No. GM23547 awarded by the National Institute of Health. The Government has certain rights in this invention.

INTRODUCTION

1. Field of the Invention

The field of the invention is cell adhesion, particularly selectin mediated cell adhesion, as well as the treatment of disease conditions related thereto.

2. Background of the Invention

Selectin mediated binding plays an important and prominent role in a variety of biological processes. Selectins are lectin like cell adhesion molecules that mediate leukocyte-endothelial, leukocyte-leukocyte, leukocyte-platelet, platelet-endothelial and platelet-platelet interactions. One critical biological process in which selectin mediated binding plays a role is the maintenance of immune surveillance.

Maintenance of immune surveillance depends on the constant recirculation of lymphocytes from the blood through the vascular wall into the tissues and eventually back into the blood. Lymphocyte recruitment from the blood into all secondary lymphoid organs (except the spleen) as well as into many sites of chronic inflammation is mediated by a specialized post-capillary venule called a high endothelial venule. These vessels are defined by the distinct, cuboidal morphology of their endothelial cells and their luminal presentation of ligands for the leukocyte adhesion molecule, L-selectin. This lectin-like adhesion molecule is expressed on all classes of leukocytes in the blood and is responsible for the initial tethering and rolling of a leukocyte on the endothelium prior to subsequent integrin mediated firm arrest and transmigration.

Several selectin ligands have, to date, been identified. The L-selectin endothelial ligands in mouse that have been identified are: CD34, GlyCAM-1, MAdCAM-1 and sgp200. In addition, PSGL-1 has been identified as a leukocyte ligand for P-, E-, and L-selectin. Endothelial ligands for L-selectin in humans are still poorly defined. However, human CD34 and Podocalyxin-like protein (PCLP) have been shown through a variety of assays to have selectin ligand activity.

Although selectin mediated binding events play a critical role in normal physiological processes, disease conditions do exist for which it is desired to regulate or modulate, e.g. limit or prevent, the amount of selectin mediated binding that occurs. Such conditions include: acute or chronic inflammation; autoimmune and related disorders, tissue rejection during transplantation, atherosclerosis, restenosis following angioplasty, damaging thrombotic events, and the like.

As the above conditions all result from selectin mediated binding events, there is great interest in the identification of selectin ligands and the elucidation of the mechanisms underlying such binding events. There is also great interest in the identification of treatment methodologies for these and related disease conditions, as well the identification of active agents for use therein.

As such, there is continued interest in the identification of new selectin ligands and the elucidation of their role(s) in selectin mediated binding events, as well as the development of therapies for disease conditions arising from such binding events.

Relevant Literature

U.S. Pat. No. 5,705,623 describes a podocalyxin like protein expressed on glomular epithelial cells. Sassetti et al., *J. Exp. Med.* (Jun. 15, 1998) 187:1965–1975 discloses the role of human PCLP as a selectin ligand. Other references describing podocalyxin and homologues thereof include: Kershaw et al., *J. Biol. Chem.* (Jun. 20, 1997) 272: 15708–15714; Kershaw et al., *J. Biol. Chem.* (Dec. 8, 1995) 270: 29439–29446; McNagny et al., *J. Cell Biol.* (Sep. 22, 1997) 138: 1395–1407; and Kerjaschki et al., *J. Cell Biol.* (1984) 98:1591–1596. Hub & Rot, Am. J. of Pathology (March 1998) 152:749–757 and Middleton et al., *Cell.* (Oct. 31, 1997) 91:385–395 provide discussions of the role of chemokines in leukocyte trafficking.

References providing background information on L-selectin binding include: Lasky et al., *Cell* (Jun. 12, 1992) 69:927–938; Baumhueter et al., *Science* (Oct. 15, 1993) 262: 436–438; Girard & Springer, *Immunology Today* (1995) 16: 449; Rosen & Bertozzi, *Current Opinion in Cell Biology* (1994) 6: 663–673; Celi et al., *Seminars in Hematology* (1997) 34: 327–335; as well as U.S. Pat. No. 5,580,862.

SUMMARY OF THE INVENTION

Nucleic acid compositions encoding novel polypeptide products with selectin ligand and/or chemokine presenting activity, as well as the polypeptide products (endoglycans) encoded thereby and methods for producing the same, are provided. The subject polypeptide and nucleic acid compositions find use in a variety of applications, including diagnostic applications, and therapeutic agent screening applications, as well as in therapeutic applications. Also provided are methods of treating disease conditions associated with selectin mediated binding events, such as acute and chronic inflammation, autoimmune diseases and related disorders, tissue rejection and the like.

BRIEF DESCRIPTION OF THE FIGURES

FIG. 1 provides the amino acid sequence (SEQ ID NO:02) and the nucleic acid sequence (SEQ ID NO:01) of human endoglycan.

DETAILED DESCRIPTION OF THE INVENTION

Novel polypeptides (endoglycans) having selectin ligand and/or chemokine presenting activity (i.e. PCLP-2), as well as nucleic acid compositions encoding the same and methods for their preparation, are provided. The subject polypeptide and nucleic acid compositions find use in a variety of applications, including research, diagnostic, and therapeutic agent screening applications, as well as in therapeutic applications. Also provided are methods of treating disease conditions associated with selectin mediated binding events, such as acute and chronic inflammation, autoimmune diseases and related disorders, tissue rejection and the like.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Nucleic Acid Compositions

Nucleic acid compositions encoding polypeptide products (hereinafter endoglycan and described in greater detail below), as well as fragments thereof, are provided. The subject endoglycans are also known as PCLP-2 proteins. By nucleic acid composition is meant a composition comprising a sequence of DNA having an open reading frame that encodes an endoglycan polypeptide, i.e. a gene encoding a polypeptide having endoglycan activity, and is capable, under appropriate conditions, of being expressed as an endoglycan polypeptide. Also encompassed in this term are nucleic acids that are homologous, substantially similar or identical to the nucleic acids encoding endoglycan polypeptides or proteins. Thus, the subject invention provides genes encoding mammalian endoglycans, such as genes encoding human endoglycan and homologs thereof and mouse endoglycan and homologs thereof.

The coding sequence of the human endoglycan gene, i.e. the human cDNA encoding the human endoglycan protein, has the nucleic acid sequence identified as SEQ ID NO:01, infra. The coding sequence of the mouse endoglycan gene, i.e. the mouse cDNA encoding the mouse endoglycan protein, is characterized by having the following ESTs derived from it: AA049027, W13047, W36468, AA008836, W54261, AA208106, AA155174 (the EST identifiers are their Gene Bank accession numbers).

The source of homologous genes to those specifically listed above may be any mammalian species, e.g., primate species, particularly human; rodents, such as rats and mice, canines, felines, bovines, ovines, equines, etc; as well as non-mammalian species, e.g. yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 3.0 nt long, and may extend to the complete sequence that is being compared. Algorithms for sequence analysis are known in the art, such as BLAST, described in Altschul et al. (1990), *J. Mol. Biol.* 215:403–10 (using default settings). Unless indicated otherwise, the sequence similarity values reported herein were determined using the above referenced BLAST program using default settings. The sequences provided herein are essential for recognizing endoglycan related and homologous polynucleotides in database searches.

Nucleic acids encoding the endoglycan proteins and endoglycan polypeptides of the subject invention may be cDNAs or genomic DNAs, as well as fragments thereof. The term "endoglycan-gene" shall be intended to mean the open reading frame encoding specific endoglycan proteins and polypeptides, and endoglycan introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding an endoglycan protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject endoglycan proteins and polypeptides, described in greater detail infra. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The endoglycan genes of the subject invention are isolated and obtained in substantial purity, generally as other than an intact chromosome. Usually, the DNA will be obtained substantially free of other nucleic acid sequences that do not include an endoglycan sequence or fragment thereof, generally being at least about 50%, usually at least about 90% pure and are typically "recombinant", i.e. flanked by one or more nucleotides with which it is not normally associated on a naturally occurring chromosome.

In addition to the plurality of uses described in greater detail in following sections, the subject nucleic acid compositions find use in the preparation of all or a portion of the endoglycan polypeptides, as described below.

Polypeptide Compositions

Also provided by the subject invention are endoglycan polypeptides. The term polypeptide composition as used herein refers to both full length proteins as well as portions or fragments thereof. Also included in this term are variations of the naturally occurring proteins, where such variations are homologous or substantially similar to the naturally occurring protein, as described in greater detail below, be the naturally occurring protein the human protein, mouse protein, or protein from some other species which naturally expresses endoglycan, usually a mammalian species. In the following description of the subject invention, the term endoglycan is used to refer not only to the human form of the protein, but also to homologs thereof expressed in non-human species, e.g. murine, rat and other mammalian species.

The subject endoglycan protein is a sialoprotein having a mucin domain, i.e. it is a sialomucin, and as such it is a highly glycosylated glycoprotein containing a region of predominantly O-linked carbohydrate chains that are linked to serine or threonine residues. Endoglycan is a transmembrane protein having the following four distinct regions: (1) a mucin domain; (2) a cysteine-rich domain; (3) a transmembrane domain; and (4) cytoplasmic domain. In addition, endoglycan contains an extremely acidic amino terminal domain which differentiates it from PCLP, disclosed in copending application Ser. No. 09/243,560, the disclosure of which is herein incorporated by reference.

The proteins range in length from about 500 to 800, usually from about 550 to 700 and more usually from about 550 to 650 amino acid residues, and the projected molecular weight of the subject proteins based solely on the number of amino acid residues in the protein ranges from about 50 to 80, usually from about 55 to 75 and more usually from about 60 to 65 kDa. As the subject endoglycan proteins are glycoproteins, the actual molecular weight of these proteins is substantially higher than the above projected molecular weights, typically ranging from about 2 to 4 times higher than the projected molecular weight. As such, the actual molecular weight typically ranges from about 150 to 300 kDa, usually from about 150 to 250 kDa and more usually from about 175 to 225 kDa, e.g. about 200 kDa.

The mucin domain is an approximately 140 residue long amino acid stretch adjacent to the amino terminal domain (described in greater detail infra) of the protein and has a high content of serine, threonine and proline, by which is meant that the relative frequency of these specific amino acids exceeds the frequency of the remaining naturally occurring amino acids by a factor of about 2 to 5 (generally these three residues make up from about 30 to 40 and usually about 35 number % of residues in the mucin domain). The mucin domain is further characterized by dense O-glycosylation. C-terminal to the mucin domain is a cysteine rich region of about 150 amino acid residues in length in which about 3 cysteine residues are present. This region is believed to form a globular structure under physiological conditions. The cytoplasmic domain of the subject endoglycan is approximately 80 amino acid residues in length and has a 25% overall sequence identity with the cytoplasmic region of CD34, and further comprises three stretches of over 50% sequence identity with the cytoplasmic region of CD34. The amino terminal domain is approximately 170 amino acids in length and is further characterized by: (a) being rich in acidic residues, where the number % of acidic amino acid residues ranges from about 20 to 40%, usually from about 25 to 35% and in many embodiments is 30% or close to 30%; (b) having two tyrosine residues which serve as potential tyrosine sulfation sites; and being modified by a glycosaminoglycan chain. In addition to the above features, endoglycan has at least 5 potential glycosaminoglycan (GAG) attachment sites (one of which is the above mentioned site in the amino or N-terminal domain) and 3 potential N-linked glycosylation sites. The protein generally has an N-terminal cleavable signal peptide of about 30 to 35 residues in length. As such, the expressed endoglycan is post-translationally processed to produce mature endoglycan.

The subject endoglycan is further characterized by being capable of presenting dense clusters of sulfated and sialylated O-linked oligosaccharides to L-selectin. The subject endoglycan is capable of binding to E-, P-, or L-selectin, as well as recombinant L-selectin. The subject endoglycan is further characterized by being able to support tethering and rolling of lymphocytes under physiological flow conditions in vitro.

In addition to the above features, the N-terminal acidic domain of endoglycan is capable of binding to certain chemokines or chemoattractant agents, where such agents include: secondary lymphoid chemokine (SLC), MIP3α, and the like.

Of particular interest in certain embodiments is the mouse endoglycan protein, where the mouse endoglycan protein of the subject invention has an amino acid sequence encoded by the mouse endoglycan gene, described above. Of particular interest in other embodiments is the human endoglycan protein, where the human endoglycan protein of the subject invention has an amino acid sequence that is substantially the same as, or identical to, the sequence appearing as SEQ ID NO:02, infra. By substantially the same as is meant a protein having a sequence that has at least about 80%, usually at least about 90% and more usually at least about 98% sequence identity with the sequence of SED ID NO:02, as measured by BLAST, supra.

In addition to the specific endoglycan proteins described above, homologs or proteins (or fragments thereof) from other species, i.e. other animal species, are also provided, where such homologs or proteins may be from a variety of different types of species, usually mammals, e.g. rodents, such as mice, rats; domestic animals, e.g. horse, cow, dog, cat; and humans. By homolog is meant a protein having at least about 35%, usually at least about 40% and more usually at least about 60% amino acid sequence identity to the specific human endoglycan protein as identified in SEQ ID NOS: 02, where sequence identity is determined using the BLAST algorithm, supra.

The endoglycan proteins of the subject invention (e.g. human endoglycan, mouse endoglycan or homologs thereof) are present in a non-naturally occurring environment, e.g. are separated from their naturally occurring environment. In certain embodiments, the subject endoglycan protein is present in a composition that is enriched for endoglycan as compared to endoglycan in its naturally occurring environment. As such, purified endoglycan is provided, where by purified is meant that endoglycan is present in a composition that is substantially free of non endoglycan proteins, where by substantially free is meant that less than 90%, usually less than 60% and more usually less than 50% of the composition is made up of non-endoglycan proteins.

In certain embodiments of interest, the endoglycan protein is present in a composition that is substantially free of the constituents that are present in its naturally occurring environment. For example, a human endoglycan protein comprising composition according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the protein's constituents will still be present in the composition prepared from the naturally occurring source.

The endoglycan of the subject invention may also be present as an isolate, by which is meant that the endoglycan is substantially free of both non-endoglycan proteins and other naturally occurring biologic molecules, such as oligosaccharides, polynucleotides and fragments thereof, and the like, where substantially free in this instance means that less than 70%, usually less than 60% and more usually less than 50% of the composition containing the isolated endoglycan is a non-endoglycan naturally occurring biological molecule. In certain embodiments, the endoglycan is present in substantially pure form, where by substantially pure form is meant at least 95%, usually at least 97% and more usually at least 99% pure.

In many preferred embodiments, the endoglycan is present in its naturally glycosylated state, i.e. it will have the same glycosylation pattern as that found in naturally occurring endoglycan such that it is a glycoprotein. In other embodiments, the proteins are non-naturally glycosylated. By non-naturally glycosylated is meant that the protein has a glycosylation pattern, if present, which is not the same as the glycosylation pattern found in the corresponding naturally occurring protein. For example, human endoglycan of the subject invention and of this particular embodiment is characterized by having a glycosylation pattern, if it is glycosylated at all, that differs from that of naturally occurring human endoglycan. Thus, the non-naturally glycosylated endoglycan proteins of this embodiment include non-glycosylated endoglycan proteins, i.e. proteins having no covalently bound glycosyl groups.

In addition to the naturally occurring endoglycan proteins, endoglycan polypeptides which vary from the naturally occurring endoglycan proteins are also provided. By endoglycan polypeptides is meant proteins having an amino acid sequence encoded by an open reading frame (ORF) of an endoglycan gene, described supra, including the full length endoglycan protein and fragments thereof, particularly biologically active fragments and/or fragments corresponding to functional domains, e.g. the N-terminal domain, the mucin domain, etc.; and including fusions of the subject polypeptides to other proteins or parts thereof, e.g. immunoglobulin domains. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to an endoglycan protein of SEQ ID NO:02, or a homolog thereof; of at least about 10 aa, and usually at least about 15 aa, and in many embodiments at least about 50 aa in length.

Also provided by the subject invention are novel ligands having selectin binding activity. The term ligand, as used herein, refers to any compound capable of binding to a selectin receptor, particularly E-, P- and L-selectin, and as such includes proteins and peptides, oligosaccharides, and the like, as well as binding mimetics thereof, including small molecule binding mimetics thereof. The subject ligands are capable of binding to selectin receptors in a manner analogous to the binding activity of HEV derived endoglycan, and will generally comprise the mucin like domain of HEV derived endoglycan, or the functional equivalent thereof. As such, the subject ligands in many embodiments will typically at least comprise a region of dense O-linked oligosaccharides covalently bonded to serine and threonine residues of a polypeptide having an amino acid sequence of at least about 30%, usually at least about 50% and more usually at least about 70% sequence identity with the amino acid sequence of the mucin domain human endoglycan.

Preparation of Endoglycan Polypeptides

The subject endoglycans, where obtained from naturally occurring sources, are generally derived from selectin ligand presenting cells, including endothelial cells, leukocytes and platelets, where it is preferably derived in many embodimentsfrom endothelial cells of high endothelial venules (HEV) of mammalian secondary lymphoid organs, and more preferably from human tonsilar HEV. The subject endoglycans may also be derived from synthetic means, e.g. by expressing a recombinant gene encoding endoglycan, such as the polynucleotide compositions described above, in a suitable host under conditions sufficient for post-translational modification to occur in a manner that provides the expressed endoglycan with selectin binding activity. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to an endoglycan gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

Endoglycan proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae,* insect cells in combination with baculovirus vectors, or cells of a higher organism such as vertebrates, particularly mammals, e.g. COS 7 cells, may be used as the expression host cells. In some situations, it is desirable to express the endoglycan gene in eukaryotic cells, where the endoglycan protein will benefit from native folding and post-translational modifications. Small peptides can also be synthesized in the laboratory. Polypeptides that are subsets of the complete endoglycan sequence may be used to identify and investigate parts of the protein important for function.

Once the source of the protein is identified and/or prepared, e.g. a transfected host expressing the protein is prepared, the protein is then purified to produce the desired endoglycan comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express endoglycan or the expression host expressing endoglycan, and purified using HPLC, exclusion chromatography, gel electrophoresis, affinity chromatography, and the like.

Uses of the Subject Endoglycan Polypeptide and Nucleic Acid Compositions

The subject polypeptide and nucleic acid compositions find use in a variety of different applications, including diagnostic, and therapeutic agent screening/discovery/preparation applications, as well as the treatment of disease conditions associated with endoglycan activity, e.g. selectin ligand activity and/or chemokine presenting activity.

General Utility

Applications in which the subject polypeptide and nucleic acid compositions find use include: (a) the identification of endoglycan homologs; (b) as a source of novel promoter elements; (c) the identification of endoglycan expression regulatory factors; (d) as probes and primers in hybridization applications, e.g. PCR; (e) the identification of expression patterns in biological specimens; (f) the preparation of cell or animal models for endoglycan function; (g) the preparation of in vitro models for endoglycan function; etc.

Identification of Endoglycan Homologs

Homologs of endoglycan are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided endoglycan sequences, e.g. allelic variants, genetically altered versions of the gene, etc., bind to the provided endoglycan sequences under stringent hybridization conditions. By using probes, particularly labeled probes of DNA sequences, one can isolate homologous or related genes.

Identification of Novel Promoter Elements

The sequence of the 5' flanking region may be utilized for promoter elements, including enhancer binding sites, that provide for regulation in tissues where endoglycan is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Identification of Endoglycan Expression Regulatory Factors

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of endoglycan gene expression, especially in different tissues or stages of development, and to identify cis acting sequences and transacting factors that regulate or mediate endoglycan gene expression. Such transcription or translational control regions may be operably linked to an endoglycan gene in order to promote expression of wild type or altered endoglycan or other proteins of interest in cultured cells, or in embryonic, fetal or adult tissues, and for gene therapy.

Probes and Primers

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Identification of Expression Patterns in Biological Specimens

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of endoglycan gene expression in the sample.

The Preparation of Endoglycan Mutants

The sequence of an endoglycan gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of endoglycan, or to alter properties of the protein that affect its function or regulation.

Production of In Vivo Models of Endoglycan Function

The subject nucleic acids can be used to generate transgenic, non-human animals or site specific gene modifications in cell lines. Transgenic animals may be made through homologous recombination, where the normal endoglycan locus is altered. Alternatively, a nucleic acid construct is randomly integrated into the genome. Vectors for stable integration include plasmids, retroviruses and other animal viruses, YACs, and the like.

The modified cells or animals are useful in the study of endoglycan function and regulation. For example, a series of small deletions and/or substitutions may be made in the host's native endoglycan gene to determine the role of different exons in cholesterol metabolism, e.g. cholesterol ester synthesis, cholesterol absorption, etc. Specific constructs of interest include anti-sense endoglycan, which will block endoglycan expression, expression of dominant negative endoglycan mutations, and over-expression of endoglycan genes. Where an endoglycan sequence is introduced, the introduced sequence may be either a complete or partial sequence of an endoglycan gene native to the host, or may be a complete or partial endoglycan sequence that is exogenous to the host animal, e.g., a human endoglycan sequence. A detectable marker, such as lac Z, may be introduced into the endoglycan locus, where upregulation of endoglycan expression will result in an easily detected change in phenotype.

One may also provide for expression of the endoglycan gene or variants thereof in cells or tissues where it is not normally expressed, at levels not normally present in such cells or tissues, or at abnormal times of development.

DNA constructs for homologous recombination will comprise at least a portion of the endoglycan gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on endoglycan activity.

Production of In Vitro Models of Endoglycan Function

Also provided by the subject invention are in vitro models of endoglycan function, e.g. the role of endoglycan as a selectin ligand, the role of endoglycan as a chemokine presenter, etc. In in vitro models of the selectin ligand function of endoglycan, binding events between endoglycan and a selectin receptor are modulated, e.g. inhibited. The selectin receptor will generally be a receptor which binds to endoglycan under physiological conditions and is a member of the selectin family of receptors that have an amino terminal C-type lectin domain followed by an EFG-like domain, a variable number of short consensus repeats known as SCR, CRP or sushi domains, and share greater than 50% homology in their lectin and EFG domains. Of particular interest is the modulation of endoglycan selectin binding events in which the selectin is L-, P-, or E-selectin. In in vitro methods of inhibiting selectin mediated binding events, such methods typically include contacting a selectin receptor with HEV derived endoglycan and a competitor or inhibitor under conditions sufficient for selectin endoglycan binding to occur. The competitor may be any compound that is, or is suspected to be, a compound capable of specifically binding to selectin, where of particular interest in many embodiments is the use of the subject ligands described above as competitors. Depending on the particular method, one or more of, usually one of, the specified components may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

The above in vitro methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times, e.g. soluble L-selectin and ligand may be combined first, and the resultant mixture subsequently combined with substrate bound HEV derived endoglycan. Following the contact step, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound selectin-endoglycan complexes will then be detected.

A variety of assay formats may also be employed for elucidating the role of endoglycan as a presenting molecule for chemokines. For example, an ELISA format can be employed in which the N-terminal domain of endoglycan is stably associated with the surface of a solid support. The support bound endoglycan is then contacted with tagged chemokine to determine whether the chemokine binds to the N-terminal domain. Inclusion of a second chemokine under a competitive format allows the testing of a plurality of different chemokines for their ability to bind to endoglycan. From the resultant data, the chemokine presenting functionality of endoglycan can readily be determined.

The above described in vitro methods find particular use in assays designed to obtain information regarding cell adhesion in mammals, particularly endoglycan/selectin mediated cell adhesion, where such cell adhesion includes cell adhesion resulting from: leukocyte-endothelium interactions; leukocyte-leukocyte interactions; platelet-leukocyte interactions; platelet-endothelial interactions; and platelet-platelet interactions. The above described assays also find use in obtaining information regarding cellular emigration, e.g. leukocyte emigration. The above described in vitro methods also find use in screening assays designed to identify compounds that inhibit the binding of selectins to endoglycan.

Endoglycan as a Marker

The subject endoglycan protein may also be used as a marker of multipotent hematopoietic progenitors from bone marrow, blood or other physiologically derived compositions. The subject invention provides methods for identifying progenitor cells in a complex mixture of cells, perhaps in combination with the use of one or more additional markers, e.g. for the quantitation of stem/progenitor cells in harvested bone marrow or mobilized blood. The subject invention also provides for methods of purifying progenitor cells from a complex mixture and producing compositions enriched for progenitor cells. Methods of using cell surface markers in the identification and/or purification of particular cells are known in the art, being described in: U.S. Pat. Nos. 5,840,502; 5,814,440; 5,807,686; 5,677,136; 5,676,849; 5,665,557; 5,663,051; 5,646,004; 5,605,805; the disclosures of which are herein incorporated by reference. The assays and protocols described in these incorporated references need only be modified to employ the subject endoglycan as the relevant cell surface marker.

DIAGNOSTIC APPLICATIONS

Also provided are methods of diagnosing disease states associated with endoglycan activity, e.g. based on observed levels of endoglycan or the expression level of the endoglycan gene in a biological sample of interest. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal endoglycan in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of endoglycan. Biochemical studies may be performed to determine whether a sequence polymorphism in an endoglycan coding region or control regions is associated with disease. Disease associated polymorphisms may include deletion or truncation of the gene, mutations that alter expression level, that affect the activity of the protein, etc.

Changes in the promoter or enhancer sequence that may affect expression levels of endoglycan can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express endoglycan may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type endoglycan sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in endoglycan may be based on the functional or antigenic characteristics of the protein. Protein truncation assays are useful in detecting deletions that may affect the biological activity of the protein. Various immunoassays designed to detect polymorphisms in endoglycan proteins may be used in screening. Where many diverse genetic mutations lead to a particular disease phenotype, functional protein assays have proven to be effective screening tools. The activity, e.g. selectin ligand functionality, of the encoded endoglycan protein may be determined by comparison with the wild-type protein.

Diagnostic methods of the subject invention in which the level of endoglycan expression is of interest will typically involve comparison of the endoglycan nucleic acid abundance of a sample of interest with that of a control value to determine any relative differences, where the difference may be measured qualitatively and/or quantitatively, which differences are then related to the presence or absence of an abnormal endoglycan expression pattern. A variety of different methods for determining the nucleic acid abundance in a sample are known to those of skill in the art, where particular methods of interest include those described in: Pietu et al., *Genome Res.* (June 1996) 6: 492–503; Zhao et al., *Gene* (Apr. 24, 1995) 156: 207–213; Soares, *Curr. Opin. Biotechnol.*(October 1997) 8: 542–546; Raval,*J. Pharmacol Toxicol Methods* (November 1994) 32: 125–127; Chalifour et al.,*Anal. Biochem* (Feb. 1, 1994) 216: 299–304; Stolz & Tuan,*Mol. Biotechnol.* (December 19960 6: 225–230; Hong et al., *Bioscience Reports* (1982) 2: 907; and McGraw,*Anal. Biochem.* (1984) 143: 298. Also of interest are the methods disclosed in WO 97/27317, the disclosure of which is herein incorporated by reference.

As endoglycan is found on CD34+ cells, also provided by the subject invention are methods of diagnosing and subclassifying leukemias. In such methods, cells are assayed for the presence of endoglycan. The presence of endoglycan is then related the presence of leukemia, and in certain embodiments a subtype thereof. Methods of using CD34+ in the diagnosis and subclassification of leukemias are known. See U.S. Pat. No. 5,605,805, the disclosure of which is herein incorporated by reference. In the present invention, analogous methods may be employed, with the only difference being that endoglycan is employed as the cell surface marker instead of CD34$^+$.

SCREENING ASSAYS

The subject endoglycan polypeptides find use in various screening assays designed to identify therapeutic agents. The screening methods will typically be assays which provide for qualitative/quantitative measurements of the endoglycan selectin ligand and/or chemokine presenting activity in the presence of a particular candidate therapeutic agent. For example, the assay could be an assay which measures the selectin ligand activity of endoglycan in the presence and absence of a candidate inhibitor agent. The screening method may be an in vitro or in vivo format, where both formats are readily developed by those of skill in the art. Depending on the particular method, one or more of, usually one of, the components of the screening assay may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Endoglycan Nucleic Acid and Polypeptide Therapeutic Compositions

The nucleic acid compositions of the subject invention also find use as therapeutic agents in situations where one wishes to enhance endoglycan activity in a host, e.g. in a mammalian host in which endoglycan activity is sufficiently low such that a disease condition is present, etc. The endoglycan genes, gene fragments, or the encoded endoglycan protein or protein fragments are useful in gene therapy to treat disorders associated with endoglycan defects.

Expression vectors may be used to introduce the endoglycan gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or endoglycan protein may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

METHODS OF MODULATING ENDOGLYCAN ACTIVITY IN A HOST

Also provided are methods of regulating, e.g inhibiting, endoglycan activity, e.g. selectin ligand and/or chemokine presenting activity, in vivo in a host. In such methods, an effective amount of active agent that modulates the selectin binding and/or chemokine presenting activity of endoglycan is administered to the host. In alternative embodiments, an agent that inhibits chemokine-endoglycan interaction is employed. The active agent may be a variety of different endoglycan activity modulators, where the modulator may act at a variety of different target sites.

One type of active agent of interest is an agent that is capable of binding to endoglycan in a manner such that the endoglycan is no longer capable of being recognized and/or bound by a selectin receptor and/or presenting chemokines. In yet other embodiments, the active agent may be an agent that interacts with a target chemokine, e.g. SLC or MIP-3α, in a manner that inhibits chemokine-endoglycan interactions. In yet other embodiments, the active agent may be one that modulates the activity of endoglycan on CD34+ bone marrow cells, thereby promoting or arresting the development of such cells. The active agent may be a variety of different compounds, including a naturally occurring or synthetic small molecule compound, an antibody, fragment or derivative thereof, an antisense composition, and the like.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Active agents also include antibodies, both polyclonal and monoclonal, and binding fragments thereof, such as Fv, F(ab')$_2$ and Fab, where such antibodies preferably recognize a functional, e.g. the mucin or N-terminal, domain of endoglycan. Such antibodies can be prepared according to methods known to those of skill in the art, where the antibodies may be humanized to improve host acceptance.

Suitable antibodies are obtained by immunizing a host animal with peptides comprising all or a portion of a endoglycan protein, such as found in the endoglycan polypeptide compositions of the subject invention. Suitable host animals include mouse, rat sheep, goat, hamster, rabbit, etc. The origin of the protein immunogen may be mouse, human, rat, monkey etc. The host animal will generally be a different species than the immunogen, e.g. human endoglycan used to immunize mice, etc.

The immunogen may comprise the complete protein, or fragments and derivatives thereof. Preferred immunogens comprise all or a part of endoglycan, where these residues contain the post-translation modifications, such as glycosylation, found on the native endoglycan. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with endoglycan, where the endoglycan will preferably be in substantially pure form, comprising less than about 1% contaminant. The immunogen may comprise complete endoglycan, fragments or derivatives thereof. To increase the immune response of the host animal, the endoglycan may be combined with an adjuvant, where suitable adjuvants include alum, dextran, sulfate, large polymeric anions, oil & water emulsions, e.g. Freund's adjuvant, Freund's complete adjuvant, and the like. The endoglycan may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The endoglycan is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using endoglycan bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Particular antibodies of interest for inhibiting endoglycan activity include: MECA-79, 2H5 as described in Sawada et al., *Biochem Biophys. Res. Corn.* 193: 337–347; and the like.

Modulators of interest as active agents also include agents that alter the structure, usually by chemical alteration through the disruption of one or more covalent bonds, of the endoglycan, particularly the mucin domain, in a manner such that the endoglycan is no longer capable of being bound by a selectin receptor. Such agents include enzymes which cleave one or more bonds present in the endoglycan structure and thereby disrupt the structure such that it is no longer recognized by a selectin receptor. Such enzymes include: chondrointinase or the like, which degrades glycosaminoglycan chains; endopeptidases, such as O-sialoglycoprotein endopeptidase, and the like; sialidases, such as *Arthrobacter ureafaciens* sialidase, Clostridium perfringens sialidase, New Castle Disease Virus sialidase, and the like; sulfatases, such as Gal-6-sulfatase and GlcNAc-6-sulfatase and the like; proteases, such as trypsin, catalytic antibodies, and the like; fucosidases; and the like In yet other embodiments of the invention, the active agent is an agent that modulates, and generally decreases, the expression of endoglycan. Such agents include antisense reagents, e.g. DNA or RNA, expression repressing agents, and the like. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model.

A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the host, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

In yet other embodiments, the agent is an agent that post-translationally alters endoglycan in a manner such that an active endoglycan is not presented on the cell surface. Such agents include: inhibitors of glycosyl or sulfotransferases, and the like.

In yet other embodiments, the active agent will be a endoglycan competitor, where such competitors include the selectin ligands of the subject invention, described above, including soluble endoglycan and selectin binding fragments thereof, which may be derived from natural sources or synthetically produced, e.g. by recombinant DNA technology such as expression of a recombinant gene encoding endoglycan in an environment capable of post-translationally modifying the expressed recombinant endoglycan to obtain compound with endoglycan like selectin binding activity.

As mentioned above, an effective amount of the active agent is administered to the host, where "effective amount" means a dosage sufficient to produce a desired result. Generally, the desired result is at least a reduction in the amount of selectin binding as compared to a control.

In the subject methods, the active agent(s) may be administered to the host using any convenient means capable of resulting in the desired inhibition of endoglycan activity, e.g. selectin binding activity, chemokine presenting activity, etc. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal,etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving selectin-endoglycan binding interactions and/or chemokine-leukocyte interactions, particularly L-, E- or P-selectin mediated binding events. Such disease conditions include those disease conditions associated with or resulting from the homing of leukocytes to sites of inflammation, the normal homing of lymphocytes to secondary lymph organs, the interaction of platelets with activated endothelium, platelet-platelet and platelet-leukocyte interactions in the blood vascular compartment; and the like. Accordingly, specific disease conditions that may be treated with the subject methods include: acute or chronic inflammation; autoimmune and related disorders, e.g. systemic lupus erythematosus, rheumatoid arthritis, polyarteritis nodosa, polymyositis and dermatomyositis, progressive systemic sclerosis (diffuse scleroderma), glomerulonephritis, myasthenia gravis, Sjogren's syndrome, Hashimoto's disease and Graves' disease, adrenalitis, hypoparathyroidism, and associated diseases; pernicious anemia; diabetes; multiple sclerosis and related demyelinating diseases; uveitis pemphigus and pemphigoid; cirrhosis and other diseases of the liver; ulcerative colitis; myocarditis; regional enteritis; adult respiratory distress syndrome; local manifestations of drug reactions (dermatitis, etc.); inflammation-associated or allergic reaction patterns of the skin; atopic dermatitis and infantile eczema; contact dermatitis, psoriasis lichen planus; allergic enteropathies; atopic diseases, e.g. allergic rhinitis and bronchial asthma; transplant rejection (heart, kidney, lung, liver, pancreatic islet cell, others); hypersensitivity or destructive responses to infectious agents; poststreptococcal diseases e.g. cardiac manifestations of rheumatic fever, etc.; tissue rejection during transplantation; atherosclerosis; restenosis after angioplasty; damaging thrombotic events, reperfusion injury; and the like. Yet other disease conditions include those characterized by the presence of blood cell adhesion to microvascular endothelial cells, e.g. cerebral postcapillary venular endothelium, where the blood cells are typically parasitized blood cells, e.g. plasmodium falciparum infected blood cells. As such, disease conditions of interest include malaria disease conditions, e.g. cerebral malaria. In these types of conditions, adhesion events involving endoglycan is blocked by one of a number of different means, e.g. through use of blocking agents such as antibodies, by use of agent which downregulate expression of the endoglycan gene, e.g. antisense, etc.

Other disease conditions of interest include those associated with the abnormal development or proliferation of endoglycan positive hematopoietic cells, e.g. leukemia. In these disease conditions, endoglycan positive hematopoietic cells are selectively removed from the patient, e.g. ablated. In yet other disease conditions, purified endogyclan$^+$ progenitor cells are obtained, e.g. using the methods described supra, and then administered to a patient in need of hematopoietic reconstitution, e.g. following meyoablative therapy for conditions such as leukemia or lymphoma, etc.

By treatment is meant at least an amelioration of the symptoms associated with the pathological condition afflicting the host, where amelioration is used in a broad sense to refer to at least a reduction in the magnitude of a parameters e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

I. Identification and Cloning of Endoglycan

Alignment of the cytoplasmic tails of CD34 and PCLP reveals significant sequence homology. By querying the NCBI Gene Bank EST data base using the cytoplasmic tail of PCLP, we were able to identify several mouse EST's which represent the same gene and share considerable homology to PCLP and CD34. One such EST clone was obtained and sequenced to verify its identity. Using this clone as a probe, northern blots were performed on mRNA from various mouse tissues to determine the size of the transcript and its expression pattern. A single 2.5 kb transcript was detected which was abundantly expressed in the brain and to a lesser extent in heart, testes, kidney, and liver. In order to clone the full-length human cDNA clone, PCR primers were generated based on this mouse sequence which amplified a specific product from both mouse and human cDNA. A PCR assay utilizing these primers was used to screen a human brain library, which was obtained as 96 master pools of 5000 plasmid clones each. Subpools containing 100 *E. Coli* clones each were obtained from several positive master pools. Positive subpools were spread on LB plates and individual colonies were screened to obtain single positive clones. This strategy resulted in the isolation of two independent clones, the longest of which was 2.3 kb in length (see FIG. 1). This cDNA (SEQ ID NO:01) predicts a protein of 605 amino acids (SEQ ID NO:02) which contains an approximately 170 amino acid N-terminal domain consisting of 30% acidic residues as well as two tyrosines which may be sulfated. This acidic domain is followed by a 140 amino acid long mucin-like domain (35% serine, threonine and proline), a cysteine-containing domain, a predicted transmembrane segment, and an 80 amino acid long cytoplasmic tail. Other predicted features include 5 potential glycosaminoglycan (GAG) attachment sites (one in the N-terminal acidic domain), and three potential N-linked glycosylation sites. Expression of bases 1–630 of this cDNA, representing the amino-terminal acidic domain, fused to the Fc domain of human IgG1 in COS-7 cells produced a major protein band of about 70 kD which was purified on protein A-sepharose and subjected to amino-terminal sequence analysis. Glycine-33 was identified as the amino-terminus of the mature protein indicating that the preceding amino acids represent a cleavable signal peptide.

II. Production of Antibodies to Endoglycan

Two domains of endoglycan were expressed in *E. coli* as 6-His fusion proteins, purified and used to immunize rabbits. The membrane-proximal cysteine-containing domain and the cytoplasmic tail were chosen as immunogens. Also, the entire extracellular domain fused to glutathione-s-transferase was expressed in mammalian cells and purified for immunizations. All antisera react with the immunizing antigen by ELISA and western blot. In order to improve specificity, antibodies from all sera were affinity purified on antigen-coupled sepharose.

III. Expression Pattern of Human Endoglycan

Using the human endoglycan clone as a probe, northern blots were performed to determine the expression pattern of this gene in human tissues. As seen in mouse, a 2.5 kb transcript was detected predominantly in brain, while lower expression was noted in pancreas, kidney, muscle, adult and fetal liver, bone marrow, peripheral blood leukocytes, thymus, lymph node, and spleen. To show that, like CD34 and PCLP, endoglycan was expressed by endothelial cells, RT-PCR was used to detect endoglycan mRNA in cDNA derived from cultured human umbilical vein endothelial cells (HUVEC). Endoglycan mRNA was also detected in HEC purified from human tonsils by immunomagnetic selection using the MECA-79 antibody. Endothelial expression of endoglycan was confirmed by staining frozen sections of human tonsils with the anti-endoglycan antibodies described above. Staining was seen in the vascular endothelium including HEV. Immunohistochemistry on mouse brain sections revealed endoglycan expression in neuronal tissue. Particularly, intense staining was noted on Purkinje cells.

IV. Biochemical Characterization of Endoglycan

The full-length endoglycan cDNA was expressed in COS-7 cells metabolically labeled with $^{35}SO_4$, and cell lysates were analyzed by SDS-PAGE. Transfection of endoglycan but not CD34 resulted in the production of a 200 kD sulfated protein. This 200 kD band was shown to represent endoglycan by immunoprecipitation with specific antibodies. Since the predicted molecular weight of the endoglycan peptide is 65 kD, we suspect that the native molecule is extensively modified with carbohydrate. The strong incorporation of $^{35}SO_4$ (much more than CD34) lead us to suspect the presence on sulfated GAG chains and/or the sulfation of the two extracellular tyrosines.

In order to produce more material for biochemical characterization, the extracellular domain of endoglycan was fused to the Fc domain of human IgG1 (endoglycan/IgG) in order to create a soluble, secreted protein. At the same time, an IgG fusion protein was made which contained only the N-terminal acidic domain of endoglycan (N-Term/IgG). Expression and $^{35}SO_4$ labeling of these endoglycan constructs, but not expression of the IgG Fc domain alone resulted in secreted, sulfated molecules which could be purified by precipitation with anti-human IgG-agarose. The presence of chondroitin sulfate on both endoglycan constructs was demonstrated by digestion of these fusion proteins with GAG degrading enzymes. A mixture of Heparinases had no effect, but chondroitinase ABC removed the majority of the sulfate from both endoglycan fusion proteins. Notably, a low molecular weight species was unaffected by chondroitinase in both cases. This species likely contains another sulfate modification, of either carbohydrate or tyrosine. In order to demonstrate the mucin-like character of endoglycan, the fusion proteins were subjected to digestion with O-sialoglycoprotein endopeptidase (OSGE). Only the full-length fusion protein, which contains the mucin-like domain, was degraded by OSGE, demonstrating the mucin-like character of this domain.

V. Endoglycan Binds Chemokines

Many chemokines are known to contain a basic heparin-binding domain. Because of the acidic nature of the N-terminal domain of endoglycan, we investigated whether chemokines could bind this protein. This would define a potential novel mechanism of chemokine immobilization on the endothelial surface. An ELISA assay was developed in which endoglycan/IgG fusion proteins are immobilized, and the binding of FLAG-tagged SLC (secondary lymphoid chemokine) can be detected with a biotinylated anti-FLAG antibody. Using this assay, we have shown that SLC/FLAG binds to endoglycan/IgG, but not to CD34/IgG. Since CD34 and endoglycan are structurally similar except for the acidic N-terminus of endoglycan, we suspected that SLC was binding to this unique domain. To demonstrate this, the N-Term/IgG fusion protein was immobilized and shown to support a similar level of binding of SLC as the full-length protein. Specificity of binding was demonstrated by inhibition with either heparin or with SLC/FLAG. In order to determine if other chemokines could bind to endoglycan, assays were performed in which unlabeled chemokines were tested for their ability to block the binding of N-Term/IgG to SLC/FLAG. Of the small panel tested thus far, MIP3α was able to efficiently inhibit SLC/FLAG binding to endoglycan, but SDF-1α and ELC were not. These results demonstrate that some, but not all chemokines are able to bind to the amino-terminal domain of endoglycan.

VI. Detection of Endoglycan on the Surface of CD34$^+$ Cells from Bone Marrow

Both CD34 and podocalyxin are found on multipotent hematopoietic progenitors. In order to determine if endoglycan was also present on these cells, purified CD34$^+$ bone marrow cells were stained with the anti-endoglycan antibody. Virtually all of these cells were found to express both CD34 and endoglycan.

To verify this finding, RT-PCR was performed on RNA extracted from these 98% pure CD34+ cells. It was found that an endoglycan fragment was amplified from this RNA only if reverse transcriptase was used in the cDNA reactions, demonstrating the presence of endoglycan mRNA in these cells.

It is evident from the above results and discussion that endoglycan is an endothelial and/or leukocyte ligand for selectins. It is also evident that new methods of inhibiting selectin binding events and/or leukocyte emigration are provided. As such, the subject invention provides for additional means to elucidate the mechanics underlying cell trafficking. In addition, the subject invention provides new means for treating disease conditions resulting from selectin binding events and or leukocyte emigration, such as acute and chronic inflammation, and the like.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated polynucleotide comprising a nucleotide sequence that encodes a polypeptide comprising the amino acid sequence set forth in SEQ ID NO:02.

2. An isolated polynucleotide comprising the nucleotide sequence set forth in SEQ ID NO:01.

3. An isolated polynucleotide encoding endoglycan, wherein said endoglycan is modified with a glycosaminoglycan.

4. An isolated polynucleotide encoding endoglycan, wherein said endoglycan specifically binds a chemokine.

5. The polynucleotide of claim 4, wherein said chemokine is selected from the group consisting of secondary lymphoid chemokine and MIP3α.

* * * * *

SEQUENCE LISTING

<160> NUMBER OF SEQ ID NOS: 2

<210> SEQ ID NO 1
<211> LENGTH: 2269
<212> TYPE: DNA
<213> ORGANISM: human

<400> SEQUENCE: 1

| | | | | | |
|---|---|---|---|---|---|
| ccagttccgg | cacgaggacc | atgggccggc | tgctgcgggc | cgcccggctg c | cgccgctgc | 60 |
| tttcgccgct | gctgcttctg | ctggttgggg | gagcgttcct | gggtgcctgt g | tggctgggt | 120 |
| ctgatgagcc | tggcccagag | ggcctcacct | ccacctccct | gctagacctc c | tgctgccca | 180 |
| ctggcttgga | gccactggac | tcagaggagc | ctagtgagac | catgggcctg g | gagctgggc | 240 |
| tgggagcccc | tggctcaggc | ttccccagcg | aagagaatga | agagtctcgg a | ttctgcagc | 300 |
| caccacagta | cttctgggaa | gaggaggaag | agctgaatga | ctcaagtctg g | acctgggac | 360 |
| ccactgcaga | ttatgttttt | cctgacttaa | ctgagaaggc | aggttccatt g | aagacacta | 420 |
| gccaggctca | agagctgcca | aacctcccct | ctcccttgcc | caagatgaat c | tggttgagc | 480 |
| ctccctggca | tatgcctccc | agagaggagg | aagaagagga | agaggaagag g | aggagaggg | 540 |
| agaaggaaga | ggtagagaaa | caagaggagg | aggaagagga | ggagctgctc c | ctgtgaatg | 600 |
| gatcccaaga | agaagccaag | cctcaggtcc | gtgacttttc | tctcaccagc a | gcagccaga | 660 |
| ccccagggc | caccaaaagc | aggcatgaag | actccgggga | ccaggcctca t | caggtgtgg | 720 |
| aggtggagag | cagcatgggg | cccagcttgc | tgctgccttc | agtcacccca a | ctacagtga | 780 |
| ctccggggga | ccaggactcc | accagccaag | aggcagaggc | cacagtgctg c | cagctgcag | 840 |
| ggcttgggt | agagttcgag | gctcctcagg | aagcaagcga | ggaagccact g | caggagcag | 900 |
| ctggtttgtc | tggccagcac | gaggaggtgc | cggccttgcc | ttcattccct c | aaaccacag | 960 |
| ctcccagtgg | ggccgagcac | ccagatgaag | atcccttgg | ctctagaacc t | cagcctctt | 1020 |
| ccccactggc | ccctggagac | atggaactga | caccttcctc | tgctaccttg g | acaagaag | 1080 |
| atctcaacca | gcagctccta | gaagggcagg | cagctgaagc | tcaatccagg a | taccctggg | 1140 |
| attctacgca | ggtgatctgc | aaggactgga | gcaatctggc | tgggaaaaac t | acatcattc | 1200 |
| tgaacatgac | agagaacata | gactgtgagg | tgttccggca | gcaccggggg c | cacagctcc | 1260 |
| tggccctggt | ggaagaggtg | ctgccccgcc | atggcagtgg | ccaccatggg g | cctggcaca | 1320 |
| tctctctgag | caagcccagc | gagaaggagc | agcaccttct | catgacactg g | tgggcgagc | 1380 |
| aggggtggt | gcccactcaa | gatgtccttt | ccatgctggg | tgacatccgc a | ggagcctgg | 1440 |
| aggagattgg | catccagaac | tattccacaa | ccagcagctg | ccaggcgcgg g | ccagccagg | 1500 |
| tgcgcagcga | ctacggcacg | ctcttcgtgg | tgctggtggt | cattggggcc a | tctgcatca | 1560 |
| tcatcattgc | gcttggcctg | ctctacaact | gctggcagcg | ccggctgccc a | agctcaagc | 1620 |

-continued

```
acgtgtcgca cggcgaggag ctgcgcttcg tggagaacgg ctgccacgac a accccacgc    1680 tggacgtggc cagcgacagc cagtcggaga tgcaggagaa gcaccccagc c tgaacggcg    1740 gcggggccct caacggcccg gggagctggg gggcgctcat gggggggcaag c gggacccccg   1800 aggactcgga cgtgttcgag gaggacacgc acctgtgagc gcagcgaggc g caggccgag    1860 tgggccgcca ggaccaagcg aggtggaccc cgaaacggac ggcccggagc c cgcaccagc    1920 ccgcgccta cccggccgcc cccgcgcctg gccctcggcg cgggctcctt c ccgcttccc     1980 ccgacttcac acggcggctt cggaccaact ccctcactcc cgcccgaggg g caggcctca    2040 aagcccgcct tggccccgct ttcccgcccc tgaaccccgg cccgcgggc g gcgggcgcg    2100 cttcctgcgc cccgggactc aattaaaccc gcccggagac cacgcgggcc c agcgaaaaa    2160 aaaaaaaaaa aaaaaaaaaa aaaaaaaaaa aaaaaaaaaa aaaaaaaaaa a aaaaaaaaa    2220 aaaaaaaaaa aaaaaaaaaa aaaaaaaaaa aaaaaaaaaa aaaaaaaaa              2269
```

<210> SEQ ID NO 2
<211> LENGTH: 605
<212> TYPE: PRT
<213> ORGANISM: human

<400> SEQUENCE: 2

```
Met Gly Arg Leu Leu Arg Ala Ala Arg Leu P ro Pro Leu Leu Ser Pro
 1               5                  10                  15

Leu Leu Leu Leu Val Gly Gly Ala Phe L eu Gly Ala Cys Val Ala
             20                  25                  30

Gly Ser Asp Glu Pro Gly Pro Glu Gly Leu T hr Ser Thr Ser Leu Leu
         35                  40                  45

Asp Leu Leu Pro Thr Gly Leu Glu Pro L eu Asp Ser Glu Glu Pro
     50                  55                  60

Ser Glu Thr Met Gly Leu Gly Ala Gly Leu G ly Ala Pro Gly Ser Gly
 65                  70                  75                  80

Phe Pro Ser Glu Glu Asn Glu Glu Ser Arg I le Leu Gln Pro Pro Gln
                 85                  90                  95

Tyr Phe Trp Glu Glu Glu Glu Leu Asn A sp Ser Ser Leu Asp Leu
            100                 105                 110

Gly Pro Thr Ala Asp Tyr Val Phe Pro Asp L eu Thr Glu Lys Ala Gly
        115                 120                 125

Ser Ile Glu Asp Thr Ser Gln Ala Gln Glu L eu Pro Asn Leu Pro Ser
    130                 135                 140

Pro Leu Pro Lys Met Asn Leu Val Glu Pro P ro Trp His Met Pro Pro
145                 150                 155                 160

Arg Glu Glu Glu Glu Glu Glu Glu Glu G lu Glu Arg Glu Lys Glu
                165                 170                 175

Glu Val Glu Lys Gln Glu Glu Glu Glu G lu Glu Leu Leu Pro Val
            180                 185                 190

Asn Gly Ser Gln Glu Glu Ala Lys Pro Gln V al Arg Asp Phe Ser Leu
        195                 200                 205

Thr Ser Ser Ser Gln Thr Pro Gly Ala Thr L ys Ser Arg His Glu Asp
    210                 215                 220

Ser Gly Asp Gln Ala Ser Ser Gly Val Glu V al Glu Ser Ser Met Gly
225                 230                 235                 240

Pro Ser Leu Leu Leu Pro Ser Val Thr Pro T hr Thr Val Thr Pro Gly
                245                 250                 255
```

```
Asp Gln Asp Ser Thr Ser Gln Glu Ala Glu Ala Thr Val Leu Pro Ala
            260                 265                 270

Ala Gly Leu Gly Val Glu Phe Glu Ala Pro Gln Glu Ala Ser Glu Glu
            275                 280                 285

Ala Thr Ala Gly Ala Ala Gly Leu Ser Gly Gln His Glu Glu Val Pro
            290                 295                 300

Ala Leu Pro Ser Phe Pro Gln Thr Thr Ala Pro Ser Gly Ala Glu His
305                 310                 315                 320

Pro Asp Glu Asp Pro Leu Gly Ser Arg Thr Ser Ala Ser Ser Pro Leu
            325                 330                 335

Ala Pro Gly Asp Met Glu Leu Thr Pro Ser Ser Ala Thr Leu Gly Gln
            340                 345                 350

Glu Asp Leu Asn Gln Gln Leu Leu Glu Gly Gln Ala Ala Glu Ala Gln
            355                 360                 365

Ser Arg Ile Pro Trp Asp Ser Thr Gln Val Ile Cys Lys Asp Trp Ser
    370                 375                 380

Asn Leu Ala Gly Lys Asn Tyr Ile Ile Leu Asn Met Thr Glu Asn Ile
385                 390                 395                 400

Asp Cys Glu Val Phe Arg Gln His Arg Gly Pro Gln Leu Leu Ala Leu
            405                 410                 415

Val Glu Glu Val Leu Pro Arg His Gly Ser Gly His His Gly Ala Trp
            420                 425                 430

His Ile Ser Leu Ser Lys Pro Ser Glu Lys Glu Gln His Leu Leu Met
            435                 440                 445

Thr Leu Val Gly Glu Gln Gly Val Val Pro Thr Gln Asp Val Leu Ser
    450                 455                 460

Met Leu Gly Asp Ile Arg Arg Ser Leu Glu Glu Ile Gly Ile Gln Asn
465                 470                 475                 480

Tyr Ser Thr Thr Ser Ser Cys Gln Ala Arg Ala Ser Gln Val Arg Ser
            485                 490                 495

Asp Tyr Gly Thr Leu Phe Val Val Leu Val Val Ile Gly Ala Ile Cys
            500                 505                 510

Ile Ile Ile Ile Ala Leu Gly Leu Leu Tyr Asn Cys Trp Gln Arg Arg
    515                 520                 525

Leu Pro Lys Leu Lys His Val Ser His Gly Glu Glu Leu Arg Phe Val
    530                 535                 540

Glu Asn Gly Cys His Asp Asn Pro Thr Leu Asp Val Ala Ser Asp Ser
545                 550                 555                 560

Gln Ser Glu Met Gln Glu Lys His Pro Ser Leu Asn Gly Gly Gly Ala
            565                 570                 575

Leu Asn Gly Pro Gly Ser Trp Gly Ala Leu Met Gly Gly Lys Arg Asp
            580                 585                 590

Pro Glu Asp Ser Asp Val Phe Glu Glu Asp Thr His Leu
            595                 600                 605
```